US009835545B2

(12) United States Patent
Furuya et al.

(10) Patent No.: US 9,835,545 B2
(45) Date of Patent: Dec. 5, 2017

(54) FLOW CELL AND METHOD OF MANUFACTURING FLOW CELL

(71) Applicant: AZBIL CORPORATION, Chiyoda-ku (JP)

(72) Inventors: Masashi Furuya, Chiyoda-ku (JP); Daisuke Obara, Chiyoda-ku (JP)

(73) Assignee: AZBIL CORPORATION, Chiyoda-ku (JP)

( * ) Notice: Subject to any disclaimer, the term of this patent is extended or adjusted under 35 U.S.C. 154(b) by 0 days.

(21) Appl. No.: 15/046,161

(22) Filed: Feb. 17, 2016

(65) Prior Publication Data

US 2016/0238517 A1    Aug. 18, 2016

(30) Foreign Application Priority Data

Feb. 18, 2015   (JP) ................. 2015-029996

(51) Int. Cl.

| G01N 21/75 | (2006.01) |
| G01N 33/00 | (2006.01) |
| G01N 21/05 | (2006.01) |
| G01N 15/14 | (2006.01) |
| G01N 31/00 | (2006.01) |
| G01N 15/10 | (2006.01) |
| G01N 21/64 | (2006.01) |

(52) U.S. Cl.
CPC ......... G01N 21/05 (2013.01); G01N 15/1436 (2013.01); G01N 15/1459 (2013.01); *G01N 2015/1006* (2013.01); *G01N 2021/6482* (2013.01); *G01N 2201/0806* (2013.01)

(58) Field of Classification Search
USPC ............................. 422/73, 400, 401
See application file for complete search history.

(56) References Cited

U.S. PATENT DOCUMENTS

| 3,989,381 | A | * | 11/1976 | Fulwyler | ............ | G01N 15/1436 356/338 |
| 5,085,500 | A | * | 2/1992 | Blesener | ............... | G01N 21/53 250/574 |
| 5,430,541 | A | * | 7/1995 | Sapp | ................. | G01N 21/0303 204/452 |
| 8,189,187 | B2 | | 5/2012 | Graham et al. | | |

(Continued)

*Primary Examiner* — Dean Kwak
(74) *Attorney, Agent, or Firm* — Oblon, McClelland, Maier & Neustadt, L.L.P.

(57) ABSTRACT

A flow cell includes a transparent planar member having a first principal surface and a second principal surface opposite to the first principal surface. The planar member has a through-hole that has a circular cross-sectional shape and that penetrates through the first principal surface and the second principal surface. The flow cell further includes a first lens element having a through-hole that has a circular cross-sectional shape. The first lens element is disposed on the first principal surface of the planar member such that the through-hole in the planar member communicates with the through-hole in the first lens element. The flow cell further includes a second lens element having a through-hole that has a circular cross-sectional shape. The second lens element is disposed on the second principal surface of the planar member such that the through-hole in the planar member communicates with the through-hole in the second lens element.

16 Claims, 12 Drawing Sheets

(56) References Cited

U.S. PATENT DOCUMENTS

| | | | | |
|---|---|---|---|---|
| 2004/0080744 A1* | 4/2004 | Hobbs | ............... | B01L 3/502715 356/246 |
| 2007/0064226 A1* | 3/2007 | Kolp | ..................... | G01N 21/05 356/246 |
| 2009/0245718 A1* | 10/2009 | Li | ......................... | B82Y 20/00 385/12 |
| 2010/0007879 A1* | 1/2010 | Mavliev | ............. | G01N 15/1459 356/336 |
| 2010/0290041 A1* | 11/2010 | Graham | ................. | C03B 23/04 356/246 |
| 2012/0207650 A1* | 8/2012 | Fortt | ..................... | G01N 21/05 422/255 |
| 2016/0290915 A1* | 10/2016 | Chen | ................. | G01N 15/1436 |

* cited by examiner

FLOW CELL AND METHOD OF MANUFACTURING FLOW CELL

CROSS-REFERENCE TO RELATED APPLICATIONS

This application claims priority to Japanese Application No. 2015-029996, filed Feb. 18, 2015, the entire contents of which are incorporated herein by reference.

BACKGROUND OF THE INVENTION

1. Field of the Invention

The present invention relates to detection techniques and relates to flow cells and methods of manufacturing flow cells.

2. Description of the Related Art

Flow cells for making fluids serving as samples flow therein are used in particle detection apparatuses, flow cytometers, microorganism detection apparatuses, and so on. Flow cells are transparent, and substances contained in fluids are analyzed through reactions obtained by irradiating the fluids flowing within the flow cells (e.g., refer to U.S. Pat. No. 8,189,187).

However, there exists a problem in that conventional flow cells are not easy to manufacture. Accordingly, an aspect of the present invention is directed to providing a flow cell that can be manufactured with ease and a method of manufacturing a flow cell.

SUMMARY OF THE INVENTION

An aspect of the present invention is a flow cell that includes (a) a transparent planar member having a first principal surface and a second principal surface that is opposite to the first principal surface, the planar member having a first through-hole provided therein, the first through-hole having a circular cross-sectional shape and penetrating through the first principal surface and the second principal surface; (b) a first lens element having a second through-hole provided therein, the second through-hole having a circular cross-sectional shape, the first lens element being disposed on the first principal surface of the planar member in such a manner that the first through-hole in the planar member communicates with the second through-hole in the first lens element; and (c) a second lens element having a third through-hole provided therein, the third through-hole having a circular cross-sectional shape, the second lens element being disposed on the second principal surface of the planar member in such a manner that the first through-hole in the planar member communicates with the third through-hole in the second lens element.

In the above flow cell, the planar member may have a side surface that is perpendicular to the first and second principal surfaces, and examining light for examining a substance flowing through the first through-hole may be incident on the side surface toward the first through-hole in the planar member.

In the above flow cell, inner walls of the second and third through-holes provided in the respective first and second lens elements may have a smoothness that is less than the smoothness of an inner wall of the first through-hole provided in the planar member. The second and third through-holes provided in the respective first and second lens elements may have a diameter that is smaller than the diameter of the first through-hole provided in the planar member. In addition, the first and second lens elements may have a transparency that is lower than the transparency of the planar member. The planar member may be made of silica glass, and the first and second lens elements may be made of a material different from the silica glass.

In the above flow cell, at least one of the first and second lens elements may be a spherical lens. Alternatively, at least one of the first and second lens elements may be an aspherical lens.

In the above flow cell, the planar member and the first and second lens elements may be joined by optical contact.

Another aspect of the present invention is a method of manufacturing a flow cell, and the method includes (a) preparing a transparent planar member having a first principal surface and a second principal surface that is opposite to the first principal surface, the planar member having a first through-hole provided therein, the first through-hole having a circular cross-sectional shape and penetrating through the first principal surface and the second principal surface; (b) preparing a first lens element having a second through-hole provided therein, the second through-hole having a circular cross-sectional shape; (c) preparing a second lens element having a third through-hole provided therein, the third through-hole having a circular cross-sectional shape; (d) disposing the first lens element on the first principal surface of the planar member in such a manner that the first through-hole in the planar member communicates with the second through-hole in the first lens element; and (e) disposing the second lens element on the second principal surface of the planar member in such a manner that the first through-hole in the planar member communicates with the third through-hole in the second lens element.

In the above method of manufacturing the flow cell, the planar member may have a side surface that is perpendicular to the first and second principal surfaces, and in the manufactured flow cell, examining light for examining a substance flowing through the first through-hole may be incident on the side surface toward the first through-hole in the planar member.

In the above method of manufacturing the flow cell, inner walls of the second and third through-holes provided in the respective first and second lens elements may have a smoothness that is less than the smoothness of an inner wall of the first through-hole provided in the planar member. The second and third through-holes provided in the respective first and second lens elements may have a diameter that is smaller than the diameter of the first through-hole provided in the planar member. In addition, the first and second lens elements may have a transparency that is lower than the transparency of the planar member. The planar member may be made of silica glass, and the first and second lens elements may be made of a material different from the silica glass.

In the above method of manufacturing the flow cell, at least one of the first and second lens elements may be a spherical lens. Alternatively, at least one of the first and second lens elements may be an aspherical lens.

In the above method of manufacturing the flow cell, the planar member and the first and second lens elements may be joined by optical contact.

In the above method of manufacturing the flow cell, the planar member may be manufactured by stretching a glass base material having a through-hole provided therein. Furthermore, the planar member may be manufactured by being cut out from the stretched glass base material.

According to the present invention, a flow cell that can be manufactured with ease and a method of manufacturing a flow cell can be provided.

DESCRIPTION OF THE PREFERRED EMBODIMENTS

Figure 1:
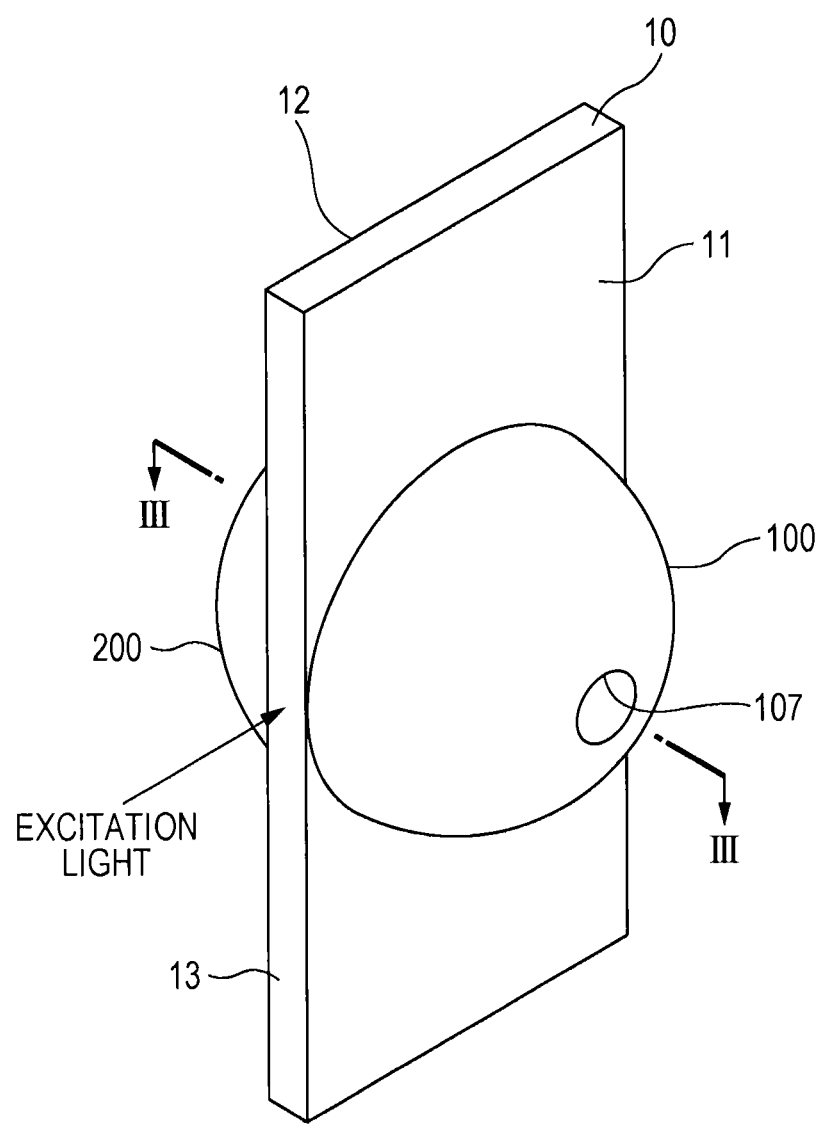
FIG. 1 is a schematic perspective view of a flow cell according to a first embodiment of the present invention.

Hereinafter, embodiments of the present invention will be described. In the following description of the drawings, identical or similar parts are indicated by identical or similar reference numerals. However, the drawings are schematic. Therefore, specific dimensions and so on are to be determined in light of the following description. In addition, it is needless to say that some parts are illustrated in different dimensional relationships or on different scales among the drawings.

First Embodiment

Figure 2:
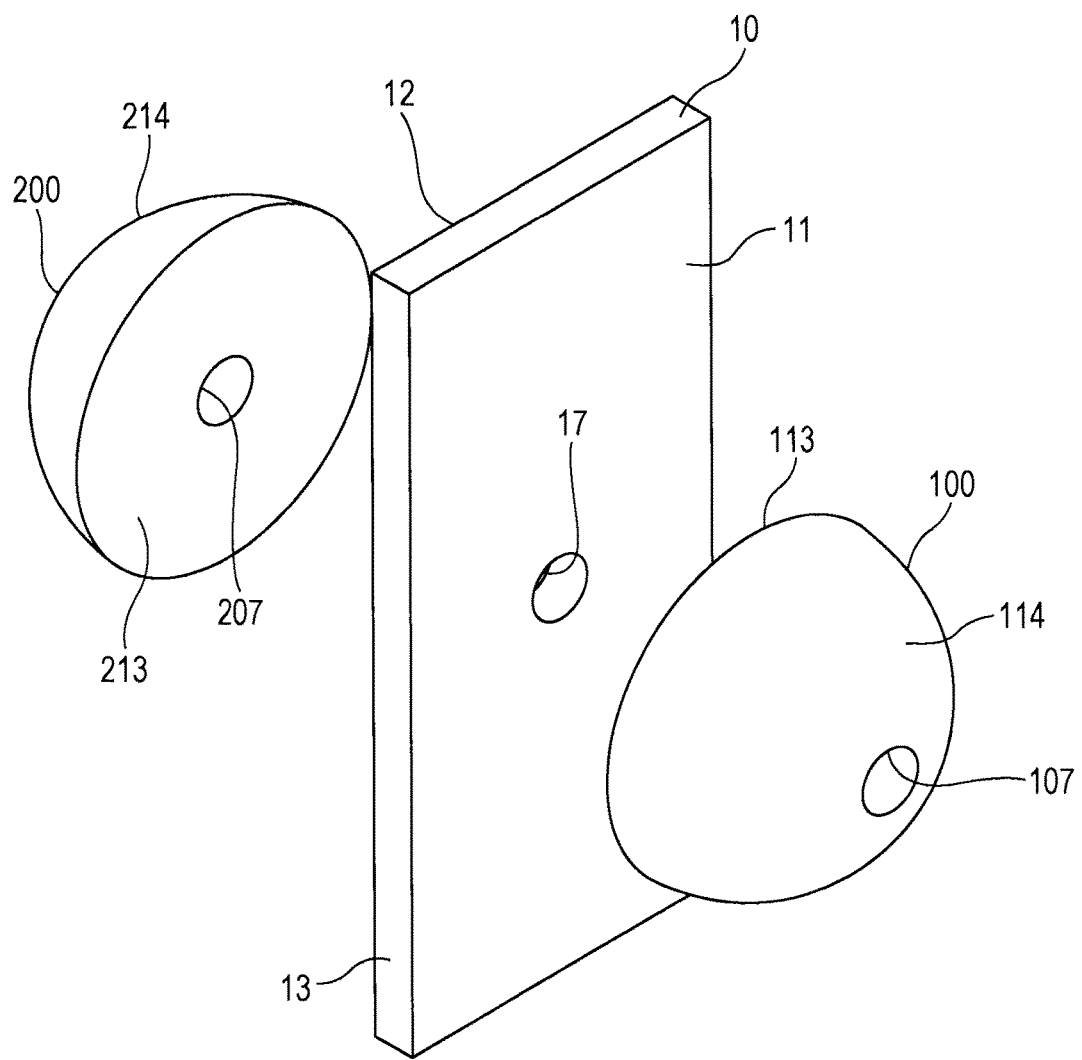
FIG. 2 is an exploded view of the flow cell according to the first embodiment of the present invention.
Figure 3:
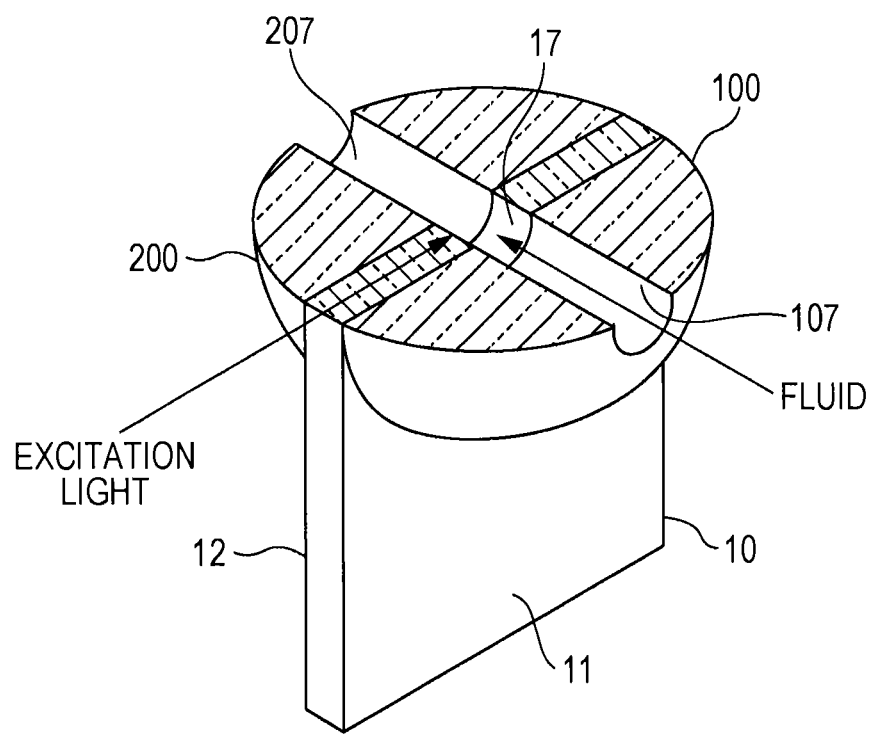
FIG. 3 is a schematic sectional view of the flow cell according to the first embodiment of the present invention, as viewed in the III-III direction of FIG. 1.

As illustrated in FIGS. 1 to 3, a flow cell according to a first embodiment of the present invention includes a transparent planar member 10 that includes a first principal surface 11 and a second principal surface 12 that is opposite to the first principal surface 11. A through-hole 17 that has a circular cross-sectional shape and that penetrates through the first principal surface 11 and the second principal surface 12 is provided in the planar member 10. The flow cell further includes a first lens element 100 in which a through-hole 107 having a circular cross-sectional shape is provided. The first lens element 100 is disposed on the first principal surface 11 of the planar member 10 in such a manner that the through-hole 17 in the planar member 10 communicates with the through-hole 107 in the first lens element 100. The flow cell further includes a second lens element 200 in which a through-hole 207 having a circular cross-sectional shape is provided. The second lens element 200 is disposed on the second principal surface 12 of the planar member 10 in such a manner that the through-hole 17 in the planar member 10 communicates with the through-hole 207 in the second lens element 200.

In the flow cell according to the first embodiment, a fluid such as a liquid containing a substance to be examined flows through the through-hole 107 in the first lens element 100, the through-hole 17 in the planar member 10, and the through-hole 207 in the second lens element 200. The fluid may flow from the side of the first lens element 100 toward the side of the second lens element 200, or may flow from the side of the second lens element 200 toward the side of the first lens element 100.

Substances to be examined include, for example, particles and cells. Particles include biological materials including microorganisms or the like, chemical materials, and dust such as waste, dirt, and soil. Examples of microorganisms include bacteria and fungi. Examples of bacteria include Gram-negative bacteria and Gram-positive bacteria. Examples of Gram-negative bacteria include colon bacilli. Examples of Gram-positive bacteria include *Staphylococcus epidermidis, Bacillus subtilis*, micrococci, and Corynebacteria. Examples of fungi include aspergilli such as black mold. However, microorganisms are not limited to the above.

When fluorescent particles such as microorganisms are contained in a fluid, the particles generate fluorescence upon being irradiated with excitation light. For example, riboflavin, flavin nucleotide (FMN), flavin adenine dinucleotide (FAD), nicotinamide adenine dinucleotide phosphate (NAD(P)H), pyridoxamine, pyridoxal-5'-phosphate, pyridoxine, tryptophan, tyrosine, phenylalanine, and so on contained in microorganisms generate fluorescence.

Excitation light serving as examining light for detecting particles flowing within the flow cell enters, for example, through a side surface 13 of the planar member 10 toward the through-hole 17 serving as an examination region and is focused inside the through-hole 17. In addition, the excitation light is incident, for example, normally on the side surface 13 of the planar member 10.

The first principal surface 11 and the second principal surface 12 of the planar member 10 are rectangular in shape, for example. The shape of the first principal surface 11 and the second principal surface 12 may be tailored to the shape of a holder for the flow cell. The side surface 13 of the planar member 10 is perpendicular to the first and second principal surfaces 11 and 12. The diameter of the through-hole 17 provided in the planar member 10 is, but is not limited to be, less than 1 mm, for example. The through-hole 17 extends perpendicularly with respect to the first and second principal surfaces 11 and 12. The planar member 10 is made, for example, of silica glass that is transparent to the excitation light for the fluorescent particles flowing through the through-hole 17. The side surface 13 of the planar member 10 to be irradiated with the excitation light preferably has a high smoothness. The fluorescent particles irradiated with the excitation light inside the through-hole 17 generate fluorescence, and scattered light is produced in the fluorescent particles.

The first and second lens elements 100 and 200 are, for example, hemispherical lenses, through which the fluorescence and the scattered light that are generated in the fluorescent particles irradiated with the excitation light in the through-hole 17 in the planar member 10 pass. The first lens element 100 has a base surface 113 and a spherical surface 114. The second lens element 200 has a base surface 213 and a spherical surface 214. The outer diameter of the base surfaces 113 and 213 of the respective first and second lens elements 100 and 200 may be greater than, equal to, or smaller than the width of the first principal surface 11 and the second principal surface 12 of the planar member 10. For example, the centers of the circular base surfaces 113 and 213 of the respective first and second lens elements 100 and 200 coincide with the center of the circular through-hole 17 provided in the planar member 10. The first and second lens elements 100 and 200 are made of silica glass, for example. Alternatively, the first and second lens elements 100 and 200 may be made, for example, of optical glass different from silica glass or of a transparent resin such as polymethyl methacrylate (PMMA) resin.

The first and second lens elements 100 and 200, which are hemispherical lenses, may each be a lens obtained by halving a perfect sphere. Alternatively, the first and second lens elements 100 and 200, which are hemispherical lenses, may each be a convex lens member having a curvature and a thickness selected such that the fluorescence and the scattered light generated at the intersection of the examining light and the through-hole 17 are incident normally on the surfaces of the respective first and second lens elements 100 and 200.

The fluorescence and the scattered light that are generated in the through-hole 17 in the planar member 10 of the flow cell and that travel toward the first lens element 100 are emitted through the surface of the first lens element 100. In the flow cell, when the thickness of the planar member 10 is less than the thickness of the first lens element 100, the fluorescence and the scattered light generated at the focal point of the examining light are incident substantially normally on the surface of the first lens element 100, which is a hemispherical lens. Thus, the fluorescence and the scattered light are emitted through the surface of the first lens element 100 with little reflection or refraction at the surface of the first lens element 100.

The fluorescence and the scattered light that are generated in the through-hole 17 in the planar member 10 of the flow cell and that travel toward the second lens element 200 are emitted through the surface of the second lens element 200. In the flow cell, when the thickness of the planar member 10 is less than the thickness of the second lens element 200, the fluorescence and the scattered light generated at the focal point of the examining light are incident substantially normally on the surface of the second lens element 200, which is a hemispherical lens. Thus, the fluorescence and the scattered light are emitted through the surface of the second lens element 200 with little reflection or refraction at the surface of the second lens element 200.

A dielectric multilayer film or a reflective film of metal or the like may be provided on at least part of the surfaces of the planar member 10 and the first and second lens elements 100 and 200.

The through-holes 107, 17, and 207 in the flow cell according to the first embodiment each have a circular cross-sectional shape and have a smooth inner wall. Therefore, it is possible to suppress air bubbles staying inside the through-holes 107, 17, and 207 or contaminant adhering to the inner walls.

The fluorescent particles flowing within the flow cell are irradiated with the excitation light inside the through-hole 17 in the planar member 10, and the fluorescence and the scattered light generated in the fluorescent particles enter the planar member 10 through the inner wall of the through-hole 17 in the planar member 10. Therefore, it is preferable that the inner wall of the through-hole 17 in the planar member 10 have high smoothness. Meanwhile, the interiors of the through-holes 107 and 207 in the respective first and second lens elements 100 and 200 are not irradiated with the excitation light. Therefore, although the smoothness of the inner walls of the through-holes 107 and 207 in the respective first and second lens elements 100 and 200 may be equal to the smoothness of the inner wall of the through-hole 17 in the planar member 10, the smoothness of the inner walls of the through-holes 107 and 207 in the respective first and second lens elements 100 and 200 may be less than the smoothness of the inner wall of the through-hole 17 in the planar member 10.

In addition, as the diameter of the through-hole 17 in the planar member 10 in which the fluorescence and the scattered light are generated is smaller, the range in which the substances to be examined flow becomes smaller with respect to the focal point of the examining light, and the possibility of a plurality of substances to be examined passing through the focal point of the examining light simultaneously is reduced. Therefore, as the diameter of the through-hole 17 is smaller, the detection resolution of the fluorescence and the scattered light tends to increase. Meanwhile, the diameters of the through-holes 107 and 207 in the respective first and second lens elements 100 and 200 that are not irradiated with the excitation light have little influence on the detection resolution of the fluorescence and the scattered light. Therefore, although the diameters of the through-holes 107 and 207 in the respective first and second lens elements 100 and 200 may be equal to the diameter of the through-hole 17 in the planar member 10, the diameters of the through-holes 107 and 207 in the respective first and second lens elements 100 and 200 may be larger than the diameter of the through-hole 17 in the planar member 10.

Furthermore, the optical intensity of the excitation light transmitted through the planar member 10 is higher than the optical intensity of the fluorescence and the scattered light generated in the planar member 10. The excitation light with high optical intensity may cause stray light, and thus the material of the planar member 10 on which the excitation light is incident is preferably a highly transparent material, such as synthetic silica. Meanwhile, the fluorescence and the scattered light have low optical intensity and are less likely to cause stray light. Therefore, although the transparency of the material of the first and second lens elements 100 and 200 may be equal to the transparency of the material of the planar member 10, the first and second lens elements 100 and 200 may be made of an inexpensive material that is less transparent than the material of the planar member 10 within a range in which the fluorescence and the scattered light can be transmitted.

The thickness of the planar member 10 along the side surface 13 may be greater than the width of the excitation light incident on the flow cell. For example, when the transparency of the first and second lens elements 100 and 200 is less than the transparency of the planar member 10 or when the transparency is reduced at the interface between the planar member 10 and the first and second lens elements 100 and 200, if the thickness of the planar member 10 along the side surface 13 is greater than the width of the excitation light incident on the flow cell, the excitation light can be prevented from being affected by a member with reduced transparency.

When the flow cell is irradiated with the excitation light normally with respect to the through-hole 17 in the planar member 10, even if the excitation light is reflected or refracted by the inner wall of the through-hole 17 in the planar member 10 to result in stray light, the stray light generated as such mainly travels along a plane that contains the intersection of the excitation light and the through-hole 17 and that is perpendicular to the direction in which the through-hole 17 extends. Therefore, by disposing a detector for the fluorescence and the scattered light so as to be offset from the plane along which the stray light travels, an influence of the stray light on the detection of the fluorescence and the scattered light can be reduced.

Figure 4:
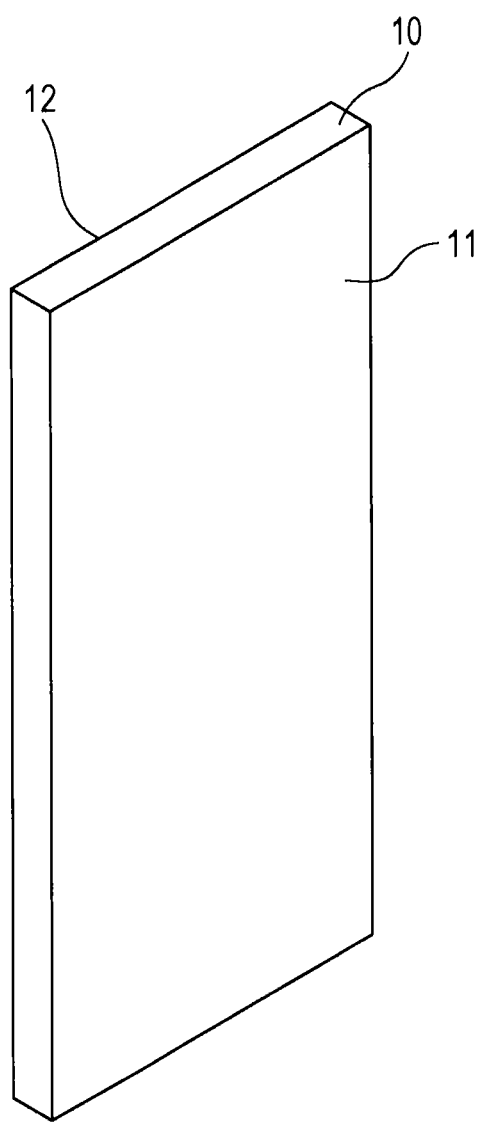
FIG. 4 is a process drawing for describing a method of manufacturing the flow cell according to the first embodiment of the present invention.
Figure 5:
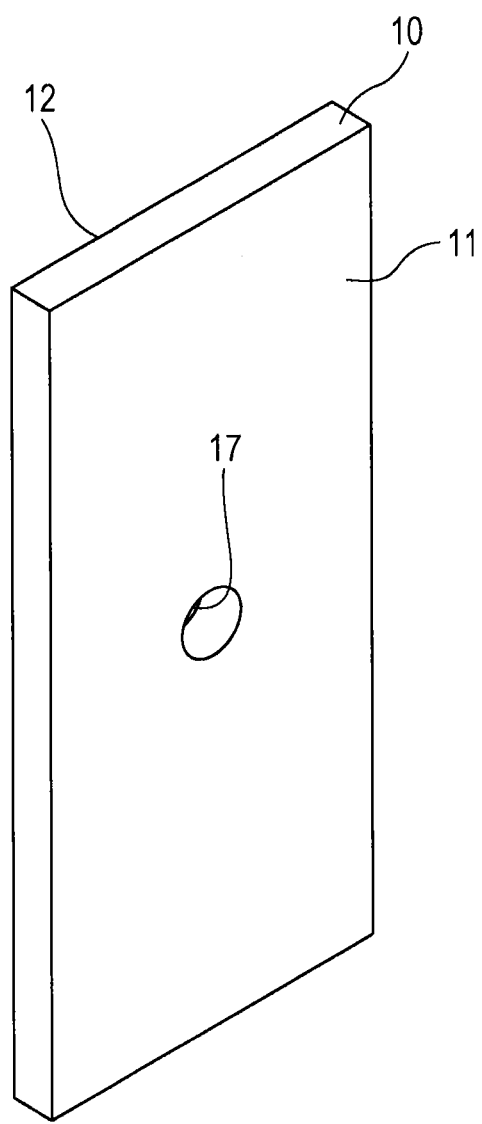
FIG. 5 is another process drawing for describing the method of manufacturing the flow cell according to the first embodiment of the present invention.
Figure 6:
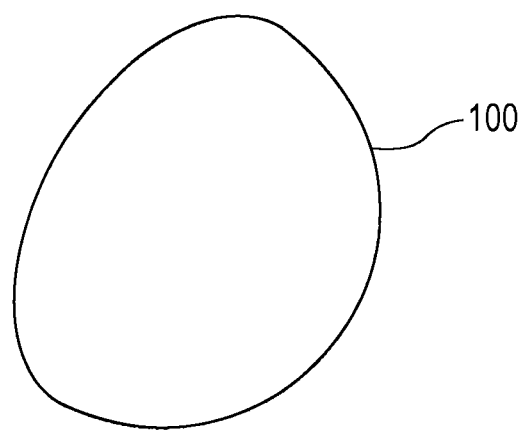
FIG. 6 is another process drawing for describing the method of manufacturing the flow cell according to the first embodiment of the present invention.
Figure 7:
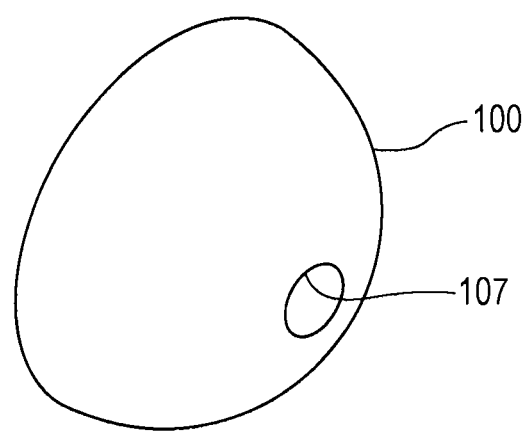
FIG. 7 is another process drawing for describing the method of manufacturing the flow cell according to the first embodiment of the present invention.
Figure 8:
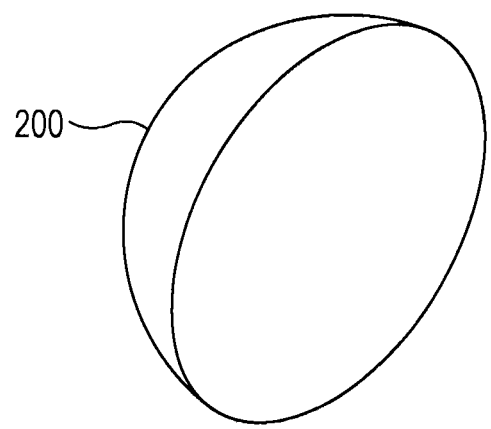
FIG. 8 is another process drawing for describing the method of manufacturing the flow cell according to the first embodiment of the present invention.
Figure 9:
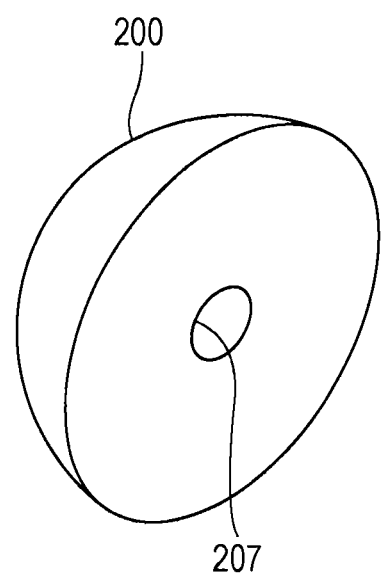
FIG. 9 is another process drawing for describing the method of manufacturing the flow cell according to the first embodiment of the present invention.

Subsequently, a method of manufacturing the flow cell according to the first embodiment will be described. As illustrated in FIG. 4, the planar member 10 is prepared; and as illustrated in FIG. 5, the through-hole 17 is provided in the planar member 10. In addition, as illustrated in FIG. 6, the first lens element 100 is prepared; and as illustrated in FIG. 7, the through-hole 107 is provided in the first lens element 100. Furthermore, as illustrated in FIG. 8, the second lens element 200 is prepared; and as illustrated in FIG. 9, the through-hole 207 is provided in the second lens element 200.

The through-holes 17, 107, and 207 can be provided through an etching technique, for example. Alternatively, the through-holes 17, 107, and 207 may be provided through drilling. After the through-holes 17, 107, and 207 are formed, the inner walls of the through-holes 17, 107, and 207 may, for example, be ground to increase the smoothness. Here, only the inner wall of the through-hole 17 may, for example, be ground to increase the smoothness.

It is easier to provide a through-hole having a highly smooth inner wall in the planar member than in the lens elements. In addition, as described above, in the manufactured flow cell, the planar member 10 is irradiated with the excitation light, but the first and second lens elements 100 and 200 are not irradiated with the excitation light. Therefore, the through-hole 17 having a highly smooth inner wall may be provided in the planar member 10, and the through-holes 107 and 207 having inner walls that are less smooth than the inner wall of the through-hole 17 may be provided in the first and second lens elements 100 and 200. Thus, the cost of manufacturing the flow cell according to the first embodiment may be reduced.

In addition, it is easier to provide a through-hole having a small diameter in the planar member than in the lens elements. Furthermore, as described above, as the diameter of the through-hole 17 in the planar member 10 is smaller, the detection resolution of the fluorescence and the scattered light in the manufactured flow cell increases, but the diameters of the through-holes 107 and 207 in the respective first and second lens elements 100 and 200 that are not irradiated with the excitation light have little influence on the detection resolution. Therefore, the through-hole 17 having a small diameter may be provided in the planar member 10, and the through-holes 107 and 207 having a larger diameter than the through-hole 17 may be provided in the respective first and second lens elements 100 and 200. Thus, the cost of manufacturing the flow cell according to the first embodiment may be reduced.

Figure 10:
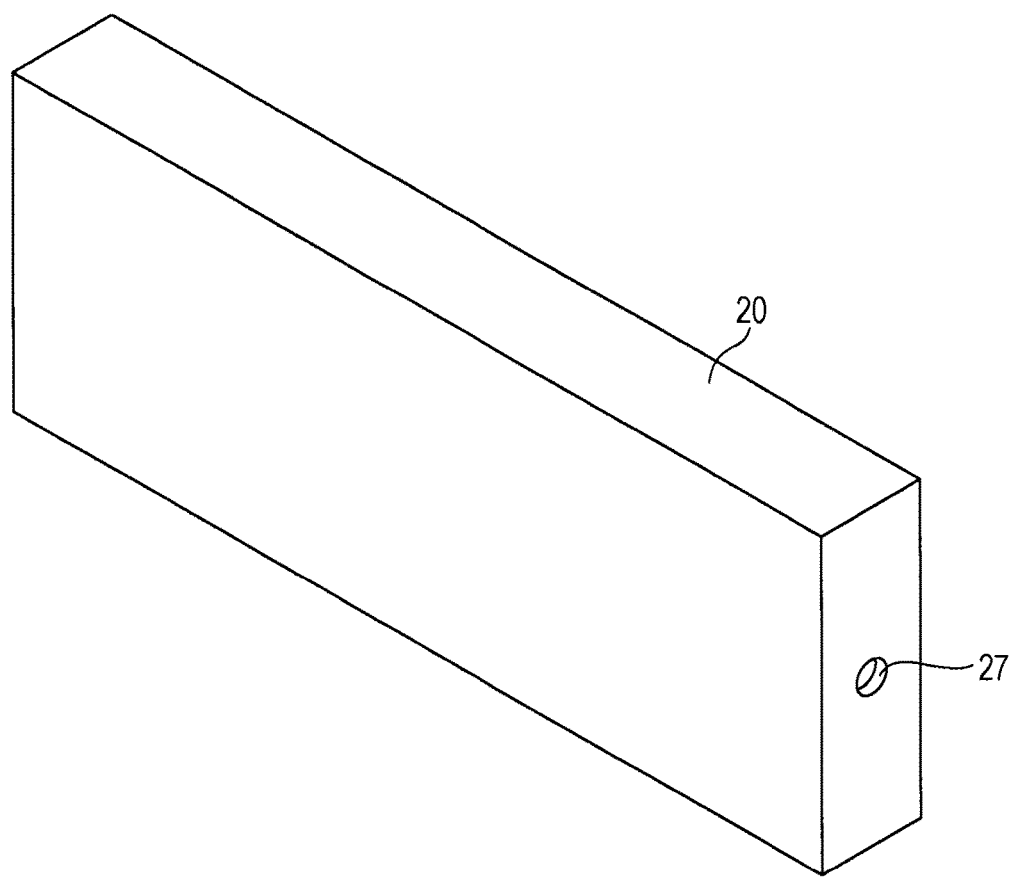
FIG. 10 is another process drawing for describing the method of manufacturing the flow cell according to the first embodiment of the present invention.

The planar member 10 in which the through-hole 17 is provided may be manufactured through a stretching technique. For example, a glass base material 20 in which a through-hole 27 having a circular cross-sectional shape is provided is prepared, as illustrated in FIG. 10. Then, by heating and stretching the glass base material 20 in the direction in which the through-hole 27 extends, the glass base material 20 is reduced in size along the cross section, and the diameter of the through-hole 27 becomes equal to that of the through-hole 17 in the planar member 10 to be manufactured illustrated in FIG. 5. Thereafter, the planar member 10 is cut out from an end portion of the stretched glass base material 20. The cut-out planar member 10 may be ground.

The planar member 10 and the first and second lens elements 100 and 200 illustrated in FIG. 2 are positioned in such a manner that the through-holes 107, 17, and 207 communicate with one another and are joined by optical contact, for example. Alternatively, the planar member 10 and the first and second lens elements 100 and 200 may be bonded through an optical adhesive or the like. In this manner, the flow cell according to the first embodiment is obtained.

According to the method of manufacturing the flow cell according to the first embodiment described thus far, by affixing the planar member 10 and the first and second lens elements 100 and 200, a flow cell that includes a lens portion having a three-dimensional shape that is hard to achieve through casting can be manufactured.

In addition, when a through-hole having an inner wall with a sharp corner is to be formed in a member, a crack or a gap tends to be generated at the sharp corner. In contrast, in the method of manufacturing the flow cell according to the first embodiment, the through-holes 17, 107, and 207 having a circular cross-sectional shape are formed, and thus generation of a crack or a gap in the inner walls of the through-holes 17, 107, and 207 can be suppressed.

Furthermore, it is more difficult to provide a through-hole having a highly smooth inner wall as the diameter of the through-hole is smaller and as the thickness of the member is greater. Therefore, it is difficult to provide a through-hole having a small diameter in a base material of a flow cell after the base material of the flow cell is formed through casting and then to increase the smoothness of the inner wall through grinding or the like. In contrast, according to the method of manufacturing the flow cell according to the first embodiment, as the planar member 10 and the first and second lens elements 100 and 200 in which the respective through-holes 17, 107, and 207 are provided in advance are affixed together, it is possible to reduce the diameter of the through-hole 17 that is irradiated with the excitation light and to increase the smoothness of the inner wall.

Second Embodiment

Figure 11:
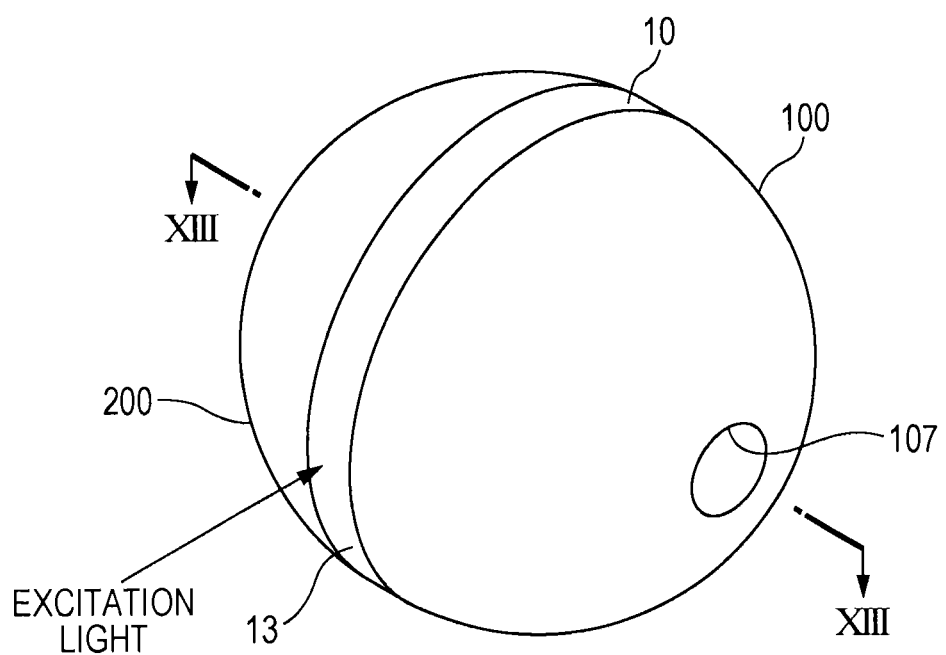
FIG. 11 is a schematic perspective view of a flow cell according to a second embodiment of the present invention.
Figure 12:
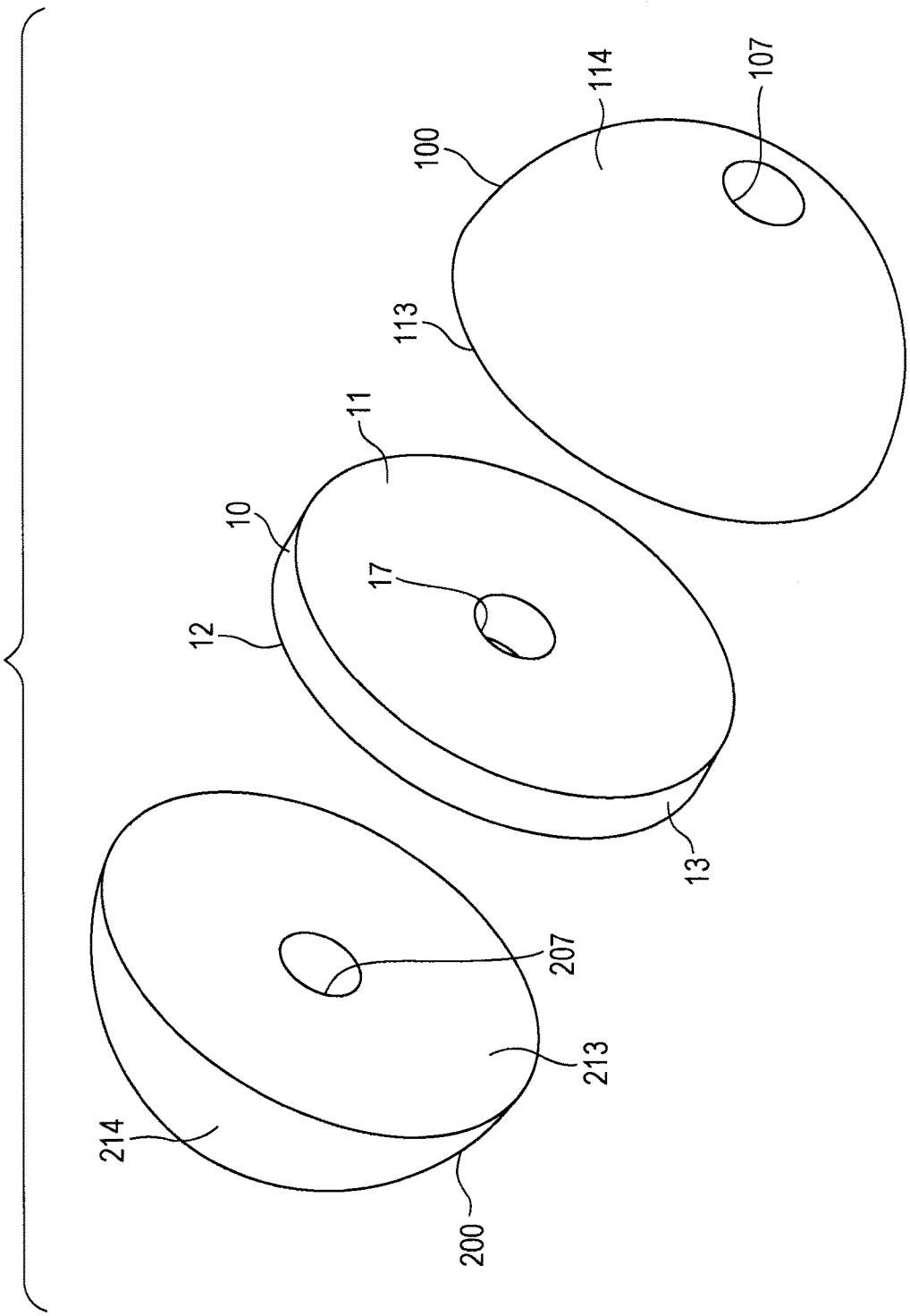
FIG. 12 is an exploded view of the flow cell according to the second embodiment of the present invention.
Figure 13:
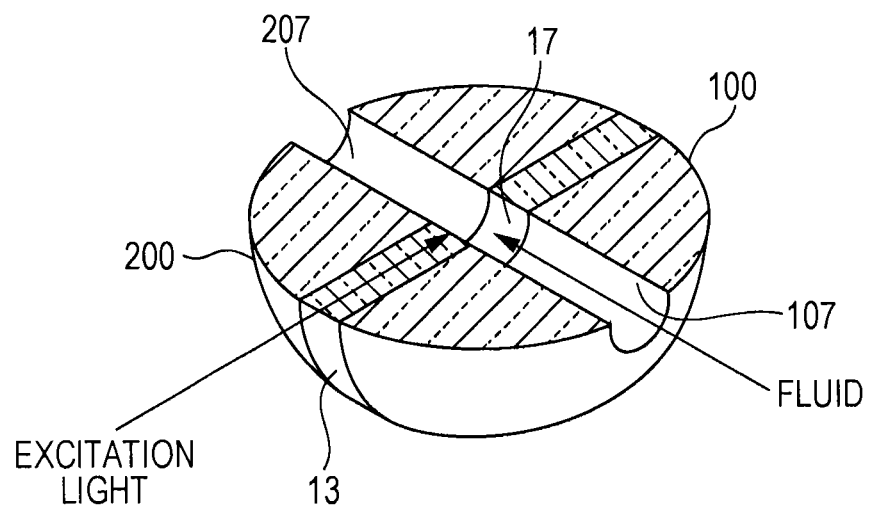
FIG. 13 is a schematic sectional view of the flow cell according to the second embodiment of the present invention, as viewed in the XIII-XIII direction of FIG. 11.

As illustrated in FIGS. 11 to 13, a flow cell according to a second embodiment of the present invention includes a planar member 10 having a circular first principal surface 11 and a circular second principal surface 12. Thus, a side surface 13 of the planar member 10 is annular. The outer diameters of the first principal surface 11 and the second principal surface 12 of the planar member 10 may be greater than, equal to, or smaller than the outer diameters of the base surfaces 113 and 213 of the respective first and second lens elements 100 and 200. Other constituent elements are the same as those of the first embodiment.

Figure 14:
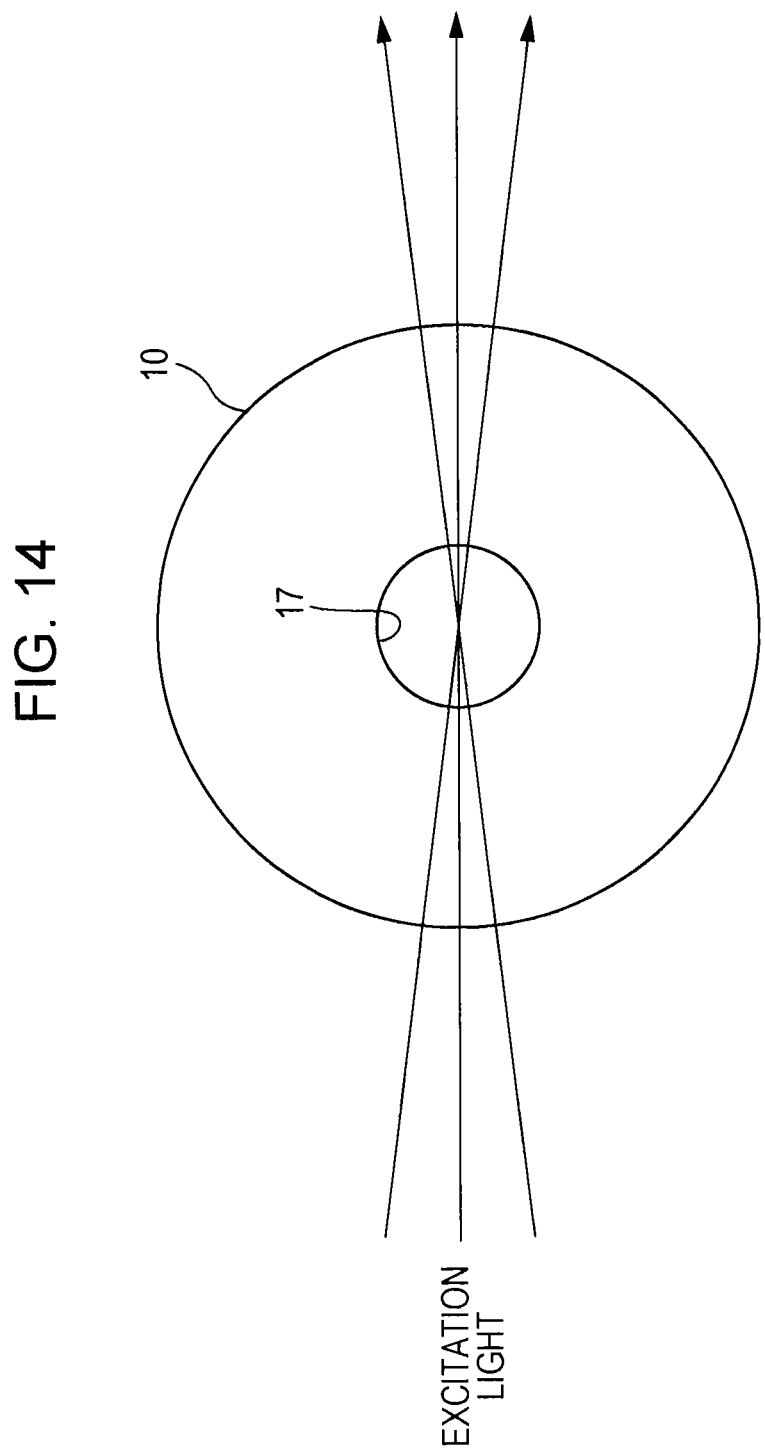
FIG. 14 is a schematic sectional view of the flow cell according to the second embodiment of the present invention.

When the outer peripheral shape of the planar member 10 and the cross-sectional shape of the through-hole 17 are circular, if the flow cell is irradiated with the excitation light such that the excitation light is focused at the center of the through-hole 17, the excitation light is incident normally on the side surface 13 of the planar member 10 and on the inner wall of the through-hole 17, as illustrated in FIG. 14.

Therefore, the excitation light can be focused in the through-hole 17 without being affected by the refractive index of the planar member 10.

Other Embodiments

The present invention has been described through embodiments as in the above, but it is not to be understood that the description and the drawings that constitute part of the present disclose limit the present invention. From the present disclose, various alternative embodiments, examples, and implementation techniques should become apparent to a person skilled in the art. For example, in the first embodiment, as illustrated in FIG. 1, an example is illustrated in which the first and second lens elements 100 and 200 are hemispherical lenses through which the fluorescence and the scattered light generated in the fluorescent particles irradiated with the excitation light in the through-hole 17 in the planar member 10 pass. However, the first and second lens elements may condense, collimate, or diffuse the fluorescence and the scattered light. Whether the fluorescence and the scattered light are to be condensed, collimated, or diffused is determined as appropriate in accordance with the detection optical system for the fluorescence and the scattered light. In addition, the first and second lens elements may be aspherical lenses having a paraboloidal surface. Alternatively, the first and second lens elements may be conical, frustoconical, or cylindrical, or may have any other desired curved surface. Furthermore, only the fluorescence may be detected, or only the scattered light may be detected. In this manner, it is to be understood that the present invention encompasses various embodiments and so on that are not described herein.

Although not being limited to the following, the present invention can be applied to an optical particle detection apparatus, a flow cytometer, an optical microorganism detection apparatus, and the like.

What is claimed is:

1. A flow cell, comprising:
   a transparent planar member having a first principal surface and a second principal surface that is opposite to the first principal surface, the planar member having a first through-hole provided therein, the first through-hole having a circular cross-sectional shape and penetrating through the first principal surface and the second principal surface, wherein the first through-hole is arranged in an axis;
   a first lens element having a second through-hole provided therein, the second through-hole having the circular cross-sectional shape, the first lens element being disposed on the first principal surface of the planar member directly attached to the transparent planar member such that the first through-hole in the planar member is directly adjacent to the second through-hole in the first lens element, the first lens element including a first planar surface and a first spherical surface, the first planar surface contacting with the first principal surface of the transparent planar member, the first lens element being configured to emit, through the first spherical surface, at least one of fluorescence and scattered light that is generated in the first through-hole and that travels toward the first lens element; and
   a second lens element having a third through-hole provided therein, the third through-hole having the circular cross-sectional shape, the second lens element being disposed on the second principal surface of the planar member directly attached to the transparent planar member such that the first through-hole in the planar member is directly adjacent to the third through-hole in the second lens element;
   wherein the first through-hole, the second through-hole, and the third through-hole are forming a continuous straight path along the axis; and
   wherein the planar member and the first and second lens elements are bonded by optical contact.

2. The flow cell according to claim 1, wherein
   the planar member has a side surface that is perpendicular to the first and second principal surfaces, and
   examining light for examining a substance flowing through the first through-hole is incident on the side surface toward the first through-hole in the planar member.

3. The flow cell according to claim 1, wherein an inner wall of the first through-hole provided in the planar member is smoother than inner walls of the second and third through-holes provided in the respective first and second lens elements.

4. The flow cell according to claim 1, wherein the second and third through-holes provided in the respective first and second lens elements have a diameter that is larger than the diameter of the first through-hole provided in the planar member.

5. The flow cell according to claim 1, wherein the first and second lens elements have a transparency that is lower than the transparency of the planar member.

6. The flow cell according to claim 1, wherein
   the planar member is made of silica glass, and
   the first and second lens elements are made of a material different from the silica glass.

7. The flow cell according to claim 1, wherein at least one of the first and second lens elements is a spherical lens.

8. The flow cell according to claim 1, wherein at least one of the first and second lens elements is an aspherical lens.

9. The flow cell according to claim 1, wherein the first lens element is a hemispherical lens.

10. The flow cell according to claim 9, wherein the first lens element has a shape of a half of a perfect sphere.

11. The flow cell according to claim 1, wherein a diameter of the first through-hole does not change according to a location in the first through-hole.

12. The flow cell according to claim 1, wherein a diameter of the second through-hole does not change according to a location in the second through-hole.

13. The flow cell according to claim 1, wherein a diameter of the third through-hole does not change according to a location in the third through-hole.

14. The flow cell according to claim 1, wherein a thickness of the transparent planar member in a direction in which the first through-hole extends is less than a thickness of the first lens element in the direction.

15. The flow cell according to claim 1, wherein a thickness of the transparent planar member in a direction in which the first through-hole extends is less than a thickness of the second lens element in the direction.

16. The flow cell according to claim 1, wherein the second lens element includes a second planar surface and a second spherical surface, the second planar surface contacting with the second principal surface of the transparent planar member, the second lens element being configured to emit, through the second spherical surface, at least one of fluorescence and scattered light that are generated in the first through-hole and that travels toward the second lens element.

* * * * *